United States Patent
Sutton et al.

(10) Patent No.: US 8,096,935 B2
(45) Date of Patent: *Jan. 17, 2012

(54) PULSATILE CONTROL SYSTEM FOR A ROTARY BLOOD PUMP

(75) Inventors: Colin Neville Sutton, Newport (AU); John Campbell Woodard, Turramurra (AU)

(73) Assignee: Thoratec Corporation, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/942,908

(22) Filed: Nov. 9, 2010

(65) Prior Publication Data

US 2011/0054239 A1   Mar. 3, 2011

Related U.S. Application Data

(63) Continuation of application No. 11/801,144, filed on May 9, 2007, now Pat. No. 7,850,594.

(30) Foreign Application Priority Data

May 9, 2006  (AU) ............................... 2006902428

(51) Int. Cl.
*A61N 1/362*   (2006.01)
(52) U.S. Cl. ......................................................... 600/16
(58) Field of Classification Search ............. 318/400.34, 318/721; 320/117; 415/107; 417/356, 423.1, 417/45; 600/16, 19; 607/8, 9
See application file for complete search history.

(56) References Cited

U.S. PATENT DOCUMENTS

| | | | |
|---|---|---|---|
| 4,296,500 A | 10/1981 | Monties et al. | |
| 4,611,578 A * | 9/1986 | Heimes | 600/19 |
| 4,957,504 A | 9/1990 | Chardack | |
| 4,969,864 A * | 11/1990 | Schwarzmann et al. | 600/16 |
| 5,289,821 A | 3/1994 | Schwartz | |
| 5,728,069 A | 3/1998 | Montevecchi et al. | |
| 6,027,498 A | 2/2000 | Mutch et al. | |
| 6,066,086 A | 5/2000 | Antaki et al. | |
| 6,071,093 A | 6/2000 | Hart | |
| 6,227,797 B1 * | 5/2001 | Watterson et al. | 415/107 |
| 6,277,078 B1 | 8/2001 | Porat et al. | |
| 6,547,753 B1 | 4/2003 | Plunket et al. | |
| 6,623,420 B2 | 9/2003 | Reich et al. | |
| 6,709,382 B1 | 3/2004 | Horner | |
| 6,991,595 B2 | 1/2006 | Burke et al. | |

(Continued)

FOREIGN PATENT DOCUMENTS

AU    2006/902428    5/2006

(Continued)

OTHER PUBLICATIONS

Monties et al., "Cora Valveless Pulsatile Rotary Pumps: New Design and Control", Ann. Thorac Surg. 61, pp. 463-468 (1996).

*Primary Examiner* — George Manuel
*Assistant Examiner* — Robert N Wieland
(74) *Attorney, Agent, or Firm* — Squire, Sanders & Dempsey (US) LLP

(57) ABSTRACT

A system for controlling the speed of a rotary blood pump. The system oscillates the speed of the pump to produce pulsed pressure at the outlet of the pump. The speed is oscillated synchronously with the natural cardiac cycle. The natural cardiac cycle is determined using a pulsatility index calculated from the back EMF produced by the pump or an impedance sensor.

15 Claims, 4 Drawing Sheets

U.S. PATENT DOCUMENTS

| | | |
|---|---|---|
| 7,138,776 B1 | 11/2006 | Gauthier et al. |
| 7,645,225 B2 | 1/2010 | Medvedev et al. |
| 2001/0009645 A1 | 7/2001 | Noda |
| 2002/0183628 A1 | 12/2002 | Reich et al. |
| 2003/0092961 A1* | 5/2003 | Korakianitis et al. ........... 600/16 |
| 2004/0152944 A1 | 8/2004 | Medvedev et al. |
| 2006/0229488 A1 | 10/2006 | Ayre et al. |

FOREIGN PATENT DOCUMENTS

| | | |
|---|---|---|
| EP | 1 354 606 | 10/2003 |
| WO | WO 01/05023 | 1/2001 |
| WO | WO 2004/028593 | 4/2004 |

* cited by examiner

PULSATILE CONTROL SYSTEM FOR A ROTARY BLOOD PUMP

PRIORITY STATEMENT

This application is a continuation of U.S. application Ser. No. 11/801,144 filed May 9, 2007, which claims priority to AU 2006902428 filed May 9, 2006. The entire contents of U.S. application Ser. No. 11/801,144 is hereby incorporated by reference for all purposes.

FIELD OF THE INVENTION

The field of the present invention relates to pulsatile control systems for rotary blood pumps.

BACKGROUND OF THE INVENTION

Blood pumps have been commonly used to provide mechanical support or assistance to the left ventricles of patients. Typically, the left ventricle is responsible for pumping blood into the aorta and throughout a majority of the patient's body. Ventricular assistance has been previously been provided by an implanted blood pump, such as the Ventrassist™ rotary blood pump described in U.S. Pat. No. 6,227,797—Watterson et al.

These blood pumps generally pump blood in parallel to the normal circulatory system by removing blood directly form the left ventricle and pumping into a portion of the aorta. Generally when such a blood pump is implanted, blood may flow or be pumped by both the left ventricle and the blood pump.

Previously, these rotary blood pumps have been operated at relatively constant speeds because of the design of the pump. In the past, some efforts have been made to adjust the pumping speed to compensate for under or over-pumping of the left ventricle. However, these types of control systems often fail to sufficiently mimic the natural cardiac cycle of a patient in which the circulatory system experiences a pulsed blood flow and/or pressure.

Previously, older blood pumps relied on compression type mechanisms to provide mechanical assistance to the heart and circulatory system. These compression type blood pumps generally include a sac member and two one-way valves arranged so as to provide pulsatile outflow to the patient's circulatory system. These devices are generally prone to mechanical failure as well as thrombogenesis or blood clotting occurring around the valves. An example of these types of pulsatile blood pumps is described within U.S. Pat. No. 5,728,069—Montevecchi et al. These types of cardiac assist devices are commonly classified as first generation assist devices.

U.S. Pat. No. 6,547,753—Plunkett et al describes a heart-lung machine that includes a blood pump. The described heart-lung machine wherein the steady state blood flow exiting the artificial lung is induced to become pulsatile by the use of an elastic bladder. However, the inclusion of a compressible bladder in this system may also be a location of potential thrombogenesis and is generally not preferred for patient safety.

U.S. Pat. No. 4,296,500—Monties et al describes a rotary blood pump that may provide a pulsatile flow by the use of a rotary piston shaped like a eccentric ovoid. The rotation of the rotary piston in this pump causes the blood passing through the pump to be ejected in a pulsed pattern whilst the piston is rotated at a steady rate. The main disadvantage with this system it that the depicted configuration may subject the blood to relatively high pressures at the times of ejection and may cause haemolysis to occur the blood.

U.S. Pat. No. 4,957,504—Chardack discloses a rotary continuous flow blood pump in which the pumping speed is ramped between two preferred settings and is synchronised with either ECG data or other data from additional implanted sensors. The main disadvantage with this arrangement is that the use of additional implanted sensors increase the patient's risk of infections, complications and blood clotting.

The present invention aims to or at least address or ameliorate one or more of the disadvantages associated with the abovementioned prior art.

SUMMARY OF THE INVENTION

According to a first aspect the present invention consists in a system for controlling the speed of a rotary blood pump, wherein said system oscillates the speed of said pump to produce pulsed pressure at the outlet of said pump, wherein the speed is oscillated synchronously with the natural cardiac cycle and characterised in that the natural cardiac cycle is determined using a pulsatility index calculated from the back EMF produced by the pump.

Preferably the speed is oscillated between two speed settings.

Preferably the pump is an implanted left ventricle assist device.

According to a second aspect the present invention consists in a method for controlling the speed of a rotary blood pump, wherein said method is to oscillate the speed of said pump to produce pulsed pressure at the outlet of said pump, wherein the speed is oscillated synchronously with the natural cardiac cycle and characterised in that the natural cardiac cycle is determined using a pulsatility index calculated from the back EMF produced by the pump.

According to a third aspect the present invention consists in a system for controlling the speed of a rotary blood, wherein said speed is adjusted in accordance with a measured impedance which is indicative of the respiration rate of a patient.

Preferably said system oscillates the speed of the rotary blood pump synchronously with the measured impedance.

BRIEF DESCRIPTION OF THE DRAWINGS

Embodiments of the present invention will now be described with reference to the accompanying drawings wherein.

BRIEF DESCRIPTION OF THE PREFERRED EMBODIMENTS

Figure 1:
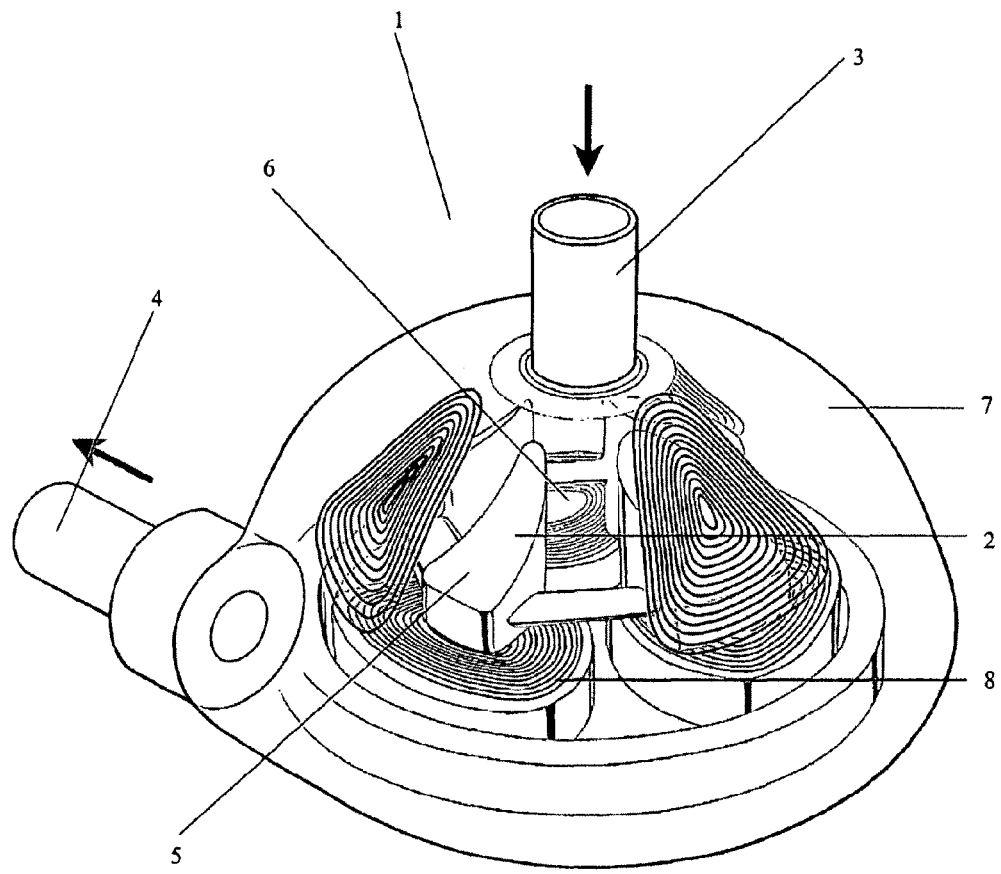
FIG. 1 depicts a cross sectional view of a preferred rotary blood pump to be used with embodiments of the present invention.
Figure 2:
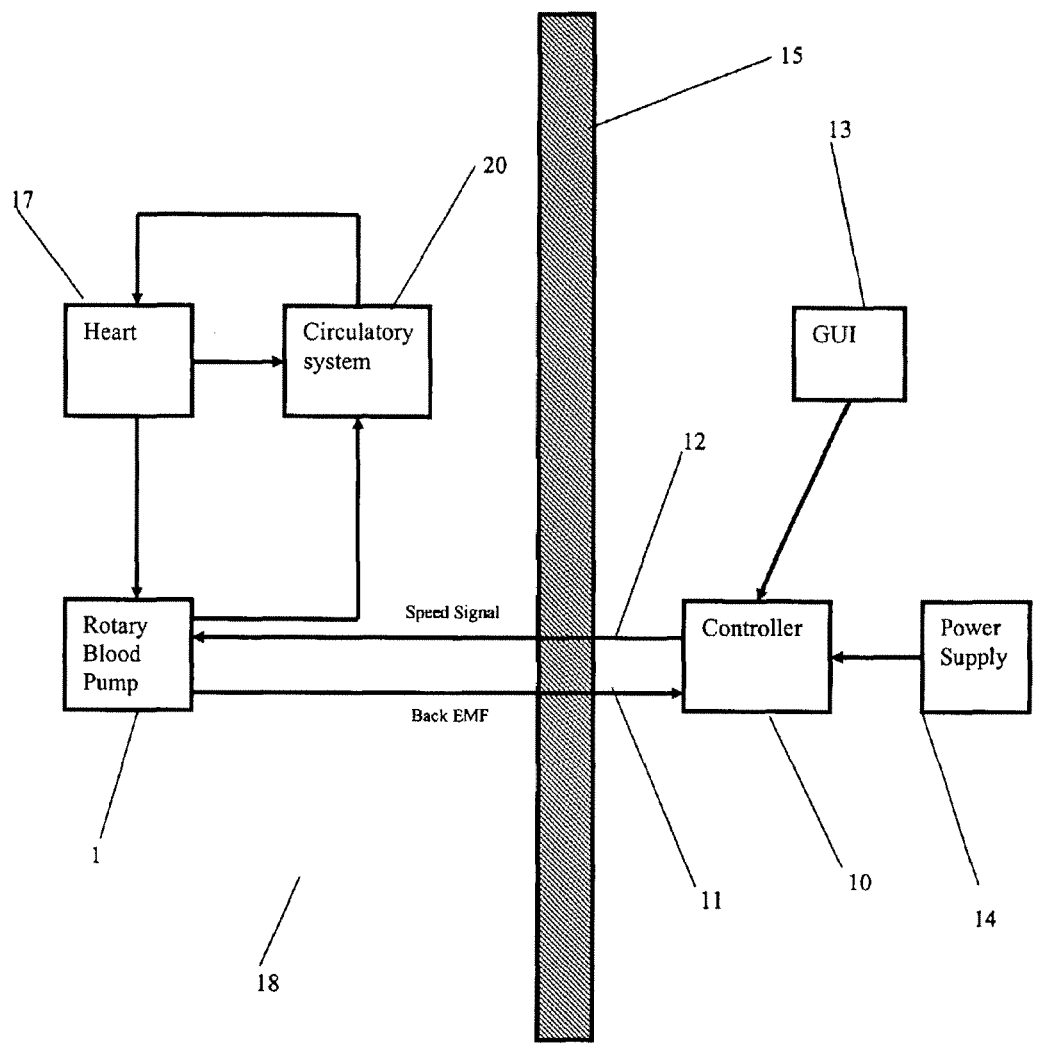
FIG. 2 depicts a diagrammatic representation of a first preferred embodiment of the present invention.
Figure 3:
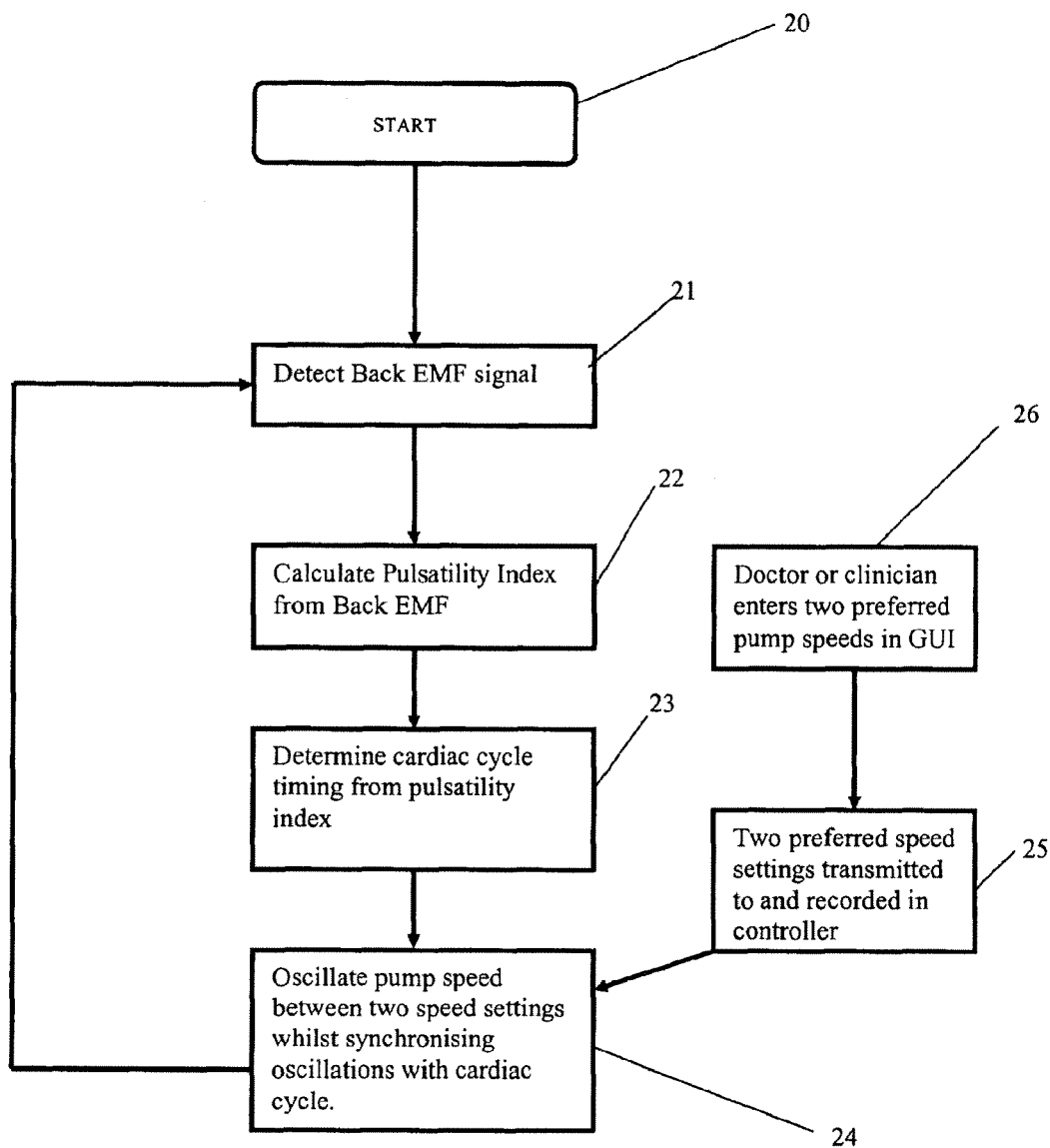
FIG. 3 depicts a flowchart of the first preferred embodiment.

A first preferred embodiment of the present invention is depicted in FIGS. 2 & 3. The first embodiment includes a controller 10 controlling and powering an implanted rotary blood pump 1. The most preferred rotary blood pump is depicted in FIG. 1.

The most preferred rotary blood pump 1, as depicted in FIG. 1, includes a hydrodynamically suspended impeller 2 comprising a set of four blades 5 joined by supports in a generally circular formation. Preferably, the impeller 2 is hydrodynamically suspended within a pumping cavity 6 within the pump housing 7. When in use, the impeller 2 is magnetically urged to rotate by the sequential firing of two sets of three stator coils 8 mounted in or on the housing above and below the impeller 2. The stator coils 8 interact with permanent magnets within each blade 5 to provide a torque force. The blood enters via the inlet 3 at the top of the pump 1 and is propelled by centrifugal force applied by the rotating impeller 2 to the outlet 4. The hydrodynamic suspension of the impeller 2 is achieved by the outer surfaces of the blades 5 being slightly inclined to produce a fluid restriction when rotated within the cavity 6. The most preferred rotary blood pump for use with the present invention or embodiments is described in detail in U.S. Pat. No. 6,227,797—Watterson et al and the description of this US patent is herein to be included within the present specification.

The most preferred rotary blood pump may also include a magnetically suspended or levitated impeller.

The first preferred embodiment of the present invention, as depicted in FIG. 2, includes an implanted rotary blood pump 1 powered and controlled by an external controller 10. Preferably, the rotary blood pump 1 is connected in parallel fluid communication with the circulatory system of the patient. In FIG. 2, the inflow or inlet of the pump 1 is connected by cannulation to natural heart 17 of the patient via the left ventricle. The normal patient circulatory system is not disconnected or interrupted by the implantation of the pump 1 and the heart 17 may continue to pump blood around the remainder of the circulatory system 20. The rotary blood pump 1 has its outflow cannula preferably connected to a portion of the aorta which is included within the circulatory system 20. When the pump 1 is operated under steady state conditions, the pump 1 continuously offloads blood from the left ventricle of the heart 17 and propels the blood into the another portion of the circulatory system such as the aorta at a relatively steady rate. Relatively steady state generally means a situation where the pump is operated at a single speed set-point by the controller but the natural cardiac motion of the heart fluctuates the actual pumping speed experienced by the pump. Thereby, the pump 1 assists a patient's heart and this system is particularly useful with patients suffering congestive heart failure which is mainly attributed to failure or insufficiency of the left ventricle.

In the depicted first preferred embodiment, the pump 1 is controlled and powered by the controller 10. The controller 10 regulates the speed 12 of the pump 1 via electrical signals transmitted by a percutaneous lead extending through the skin layer 15 of an implanted patient. Please note that electrical signals may be transmitted by alternate means including transcutaneous energy transmission systems (commonly referred to as 'TETS'). The controller 10 also preferably receives data back from the rotary blood pump 1. The information received may include back EMF data or signals which are preferably generated to the motion of the DC brushless motor design which is inherently included within the design and configuration of the most preferred rotary blood pump.

Preferably, when the impeller 2 rotates within the cavity 6, the permanent magnets within the blades 5 pass the respective stator coils 8 and induce an electrical current in said stator coils 8. This induced electrical current is detected and measured by controller 10 as a back EMF signal 11. The back EMF 11 signal or data may allow the controller 10 to accurately predict the speed of rotation of the impeller 2 as well as the position of the blades 5 of the impeller 2 at any given instance.

The controller 10 receives electrical power from an external power supply 14 and uses this supplied electrical power to power the rotary action of the pump 1. The power supply 14 may be a mains power connection or a set of batteries.

The controller 10 may also be able to be selectively connected to a personal computer (not shown) and this personal computer may run a graphical user interface 13 software (herein referred to as 'GUI'). The GUI 13 may be utilised by a patient, doctor, clinician or nursing staff to display information and statistics about the pump 1 and the condition of the patient which is received from the controller 10. The GUI 13 may also be used to input data, operating parameters and commands into the controller 10. In this first preferred embodiment, the doctor or clinician may be able to manually enter operating parameters for the pump 1 into the GUI 13 and the GUI 13 may then program these parameters into the controller 10. The controller 10 will then operate the pump 1 within these parameters.

FIG. 3 depicts a flowchart of a preferred decision tree followed by the controller 10. The flowchart starts at the first step 20 and then detects 21 the back EMF 11 received from the pump 1. The back EMF 11 is generally indicative of the pumping speed of the pump 1. The controller 1 then proceeds to the step 22, wherein the controller 10 calculates a pulsatility index from the speed of pump 1 determined from back EMF 11 data.

The controller 10 may then determine the current stage at which the natural heart 17 is in terms of its cardiac cycle 23. Specifically, it may be possible for the controller 10 to determine whether the heart 17 is currently in diastole or systole based calculation and derivation of the pulsatility index.

The final step 24 for the controller 10 is to oscillate the pumping speeds preferably between two predetermined speed values and to simultaneously synchronise these speed oscillations with the cardiac cycle or timing of the heart 1 as determined in the earlier step 23. Preferably, the oscillations may be timed so as to either prevent ventricular collapse or to maximum pumping efficiency. The pumping efficiency may be maximised as the rotary blood pump 1 may potentially be periodically at a higher speed setting, if the speed oscillations are properly timed.

Preferably, the doctor or clinician may enter two preferred pump speeds for the controller 10 to oscillate between. These predetermined speed values are entered into the GUI 13 in step 26, which may occur at anytime when the controller 10 is connected to the GUI 13. The GUI 13 then transmits the predetermined speed values to the controller 10 and these values are then recorded in the controller 10 in step 25.

Figure 4:
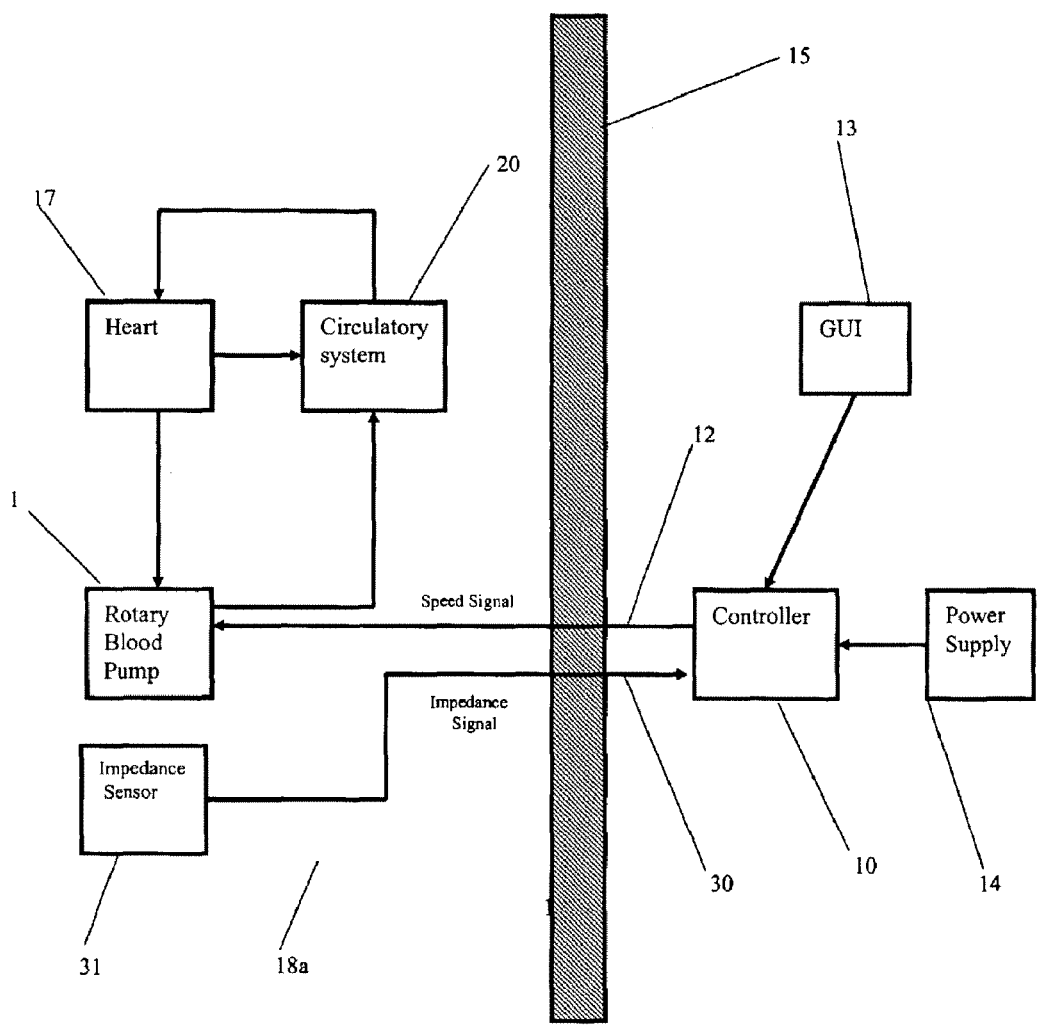
FIG. 4 depicts a diagrammatic representation of a second preferred embodiment of the present invention.

A second embodiment of the present invention as shown in FIG. 4, utilises an impedance sensor 31 instead of back EMF data 11 as in the first embodiment. The impedance sensor 31 measures the impedance across a portion of the heart. The variance in impedance is generally indicative of the breathing or respiration rate of the implanted patient. Therefore from the measured impedance the controller may be able to infer or derive the respiration rate of the patient and use this respiration rate as an analog of instantaneous metabolic rate of the patient. Hence, the impedance sensor 31 may be measuring the minute volume or minute ventilation of the patient and allowing for calculations based on the amount of air in the lungs. An advantage of using an impedance sensor, is that such an impedance sensor does not need to contact blood, thus avoiding the problems of prior art sensors that do contact blood.

The controller 2 may then use the impedance signal (information) 18*a* to alter or adjust pump speed to properly meet the patient's metabolic demands. Additionally, the controller 2 may be able to adjust the timing of the oscillations of pump speed to match the beating of the heart or the respiratory needs of the patient.

The above descriptions detail only some of the embodiments of the present invention. Modifications may be obvious to those skilled in the art and may be made without departing from the scope and spirit of the present invention.

What we claim is:

1. A system for controlling the speed of a rotary blood pump having a motor, comprising:
   an impedance sensor adapted for measuring the impedance across a portion of the heart;
   a controller configured to
      receive as input a signal produced by the impedance sensor,
      calculate a pulsatility index indicative of a diastole or systole phase of a cardiac cycle from the signal, and
      send a control signal based on the computed pulsatility index for varying the pump speed between a first and second speed so as to synchronize motor speed with the occurrence of the diastole or systole phase of the cardiac cycle.

2. The system of claim 1, wherein the controller is configured to calculate a pulsatility index indicative of a diastole or systole phase of a cardiac cycle based on a respiration rate of an implanted patient, as indicated by the received signal.

3. The system of claim 1, wherein the controller is configured to receive as input two motor speed settings.

4. The system of claim 1, wherein the controller is configured to operate at a single speed set point with fluctuations about the set point corresponding to the input first and second speeds.

5. The system of claim 1, wherein the controller is configured for varying pump speed to prevent ventricular collapse or maximize pumping efficiency.

6. A method for controlling the speed of a rotary blood pump having a motor, comprising:
   sensing a signal produced by an impedance sensor adapted for measuring the impedance across a portion of the heart;
   deteimining a parameter indicative of a diastole or systole phase of a cardiac cycle from the sensed signal; and
   varying the pump speed between a first and second motor speed based on the determined parameter so as to synchronize motor speed with the occurrence of the diastole or systole phase of the cardiac cycle.

7. The method of claim 6, further including determining a pulsatility index indicative of a diastole or systole phase of a cardiac cycle.

8. The method of claim 6, further including determining the parameter indicative of a diastole or systole phase of a cardiac cycle based on the received signal indicating a respiration rate of an implanted patient.

9. The method of claim 6, further including providing the first and second motor speeds as input to a controller for performing the method.

10. The method of claim 6, wherein the pump speed is varied to prevent ventricular collapse or maximize pumping efficiency.

11. A system for preventing ventricular collapse or maximizing pumping efficiency, comprising:
    a rotary blood pump having a motor; and
    a controller coupled to the blood pump;
    wherein the controller is configured to receive as input
       a signal produced by an impedance sensor adapted for measuring the impedance across a portion of the heart,
       calculate a parameter indicative of a diastole or systole phase of a cardiac cycle from the received signal, and
       send a control signal to the motor based on the computed parameter for varying the pump speed between a first and second speed so as to synchronize motor speed with the occurrence of the diastole or systole phase of the cardiac cycle.

12. The system of claim 11, wherein the blood pump includes a magnetically suspended, or hydro-dynamically suspended impeller.

13. The system of claim 11, wherein the controller is configured for being external of the patient.

14. The system of claim 11, wherein the controller is configured to receive as input two motor speed settings.

15. The system of claim 11, wherein the controller is configured to calculate a pulsatility index indicative of a diastole or systole phase of a cardiac cycle.

* * * * *